United States Patent [19]

Morgan

[11] Patent Number: 5,380,762
[45] Date of Patent: Jan. 10, 1995

[54] METHOD FOR CONTROLLING MACROINVERTEBRATES

[75] Inventor: Frederic L. Morgan, Cordova, Tenn.

[73] Assignee: Buckman Laboratories International, Inc., Memphis, Tenn.

[21] Appl. No.: 12,367

[22] Filed: Feb. 2, 1993

[51] Int. Cl.$^6$ ................ A01N 33/02; A01N 59/10
[52] U.S. Cl. ............................. 514/673; 424/673; 424/676
[58] Field of Search .............. 424/669, 673, 676; 514/673

[56] References Cited

U.S. PATENT DOCUMENTS

| | | | |
|---|---|---|---|
| 3,480,658 | 11/1969 | Rohr | 260/465 |
| 4,022,882 | 5/1977 | Ely | 424/80 |
| 4,148,884 | 4/1979 | Thorogood | 424/150 |
| 4,462,914 | 7/1984 | Smith | 210/755 |
| 4,917,901 | 4/1990 | Bourbon et al. | 424/673 |
| 4,970,239 | 11/1990 | Whitekettle et al. | 514/665 |
| 5,147,605 | 9/1992 | Tatsuno et al. | 422/37 |

FOREIGN PATENT DOCUMENTS

| | | | |
|---|---|---|---|
| 54-110323 | 8/1979 | Japan | 514/673 |
| WO86/05510 | 9/1986 | WIPO | |

OTHER PUBLICATIONS

Karande et al, C.A., vol. 83, (1975) 127407g.
Lisicky, C. A., vol. 80 (1974) 44506a.
Chemical Abstracts, vol. 87, No. 64075g, 1977.
Chemical Abstracts, vol. 67, No. 81493w, 1967.
Chemical Abstracts, vol. 92, No. 1670e, 1980.
Chemical Abstracts, vol. 65, No. 4577g, 1966.
Chemical Abstracts, vol. 91, No. 85169p, 1979.
Thornton, Pulp & Paper, Jun. 1989, pp. 127–129.
Nash, Time, Jan. 21, 1991, p. 63.
Doherty et al., Environmetal Pollution, vol. 51, pp. 269–313, 1988.
West Agro, Inc., Product Data Sheet, "Ethylenediamine Dihydriodide (EDDI)" dated Apr. 01, 1989.
Chemical Marketing Reporter, "Nalco Offers Defense Against Zebra Mussels," Hoffman, Jan. 7, 1991.
Derwent Abstract WPI Acc No: 88-230442/33 (1988).
Derwent Abstract WPI Acc No: 81-17954D/11 (1985).
Derwent Abstract WPI Acc No: 80-77563C/44 (1980).
Derwent Abstract WPI Acc No: 80-40417C/23 (1980).
Derwent Abstract WPI Acc No: 79-74108B/41 (1981).
Derwent Abstract WPI Acc No: 77-22793Y (1977).
Derwent Abstract WPI Acc No: 75-81450W/50 (1975).
Derwent Abstract WPI Acc No: 73-65608U/44 (1970).
Derwent Abstract WPI Acc No: 70-60102R/34 (1968).
Derwent Abstract WPI Acc No: 70-07122R/05 (1974).
Derwent Abstract WPI Acc No: 67-08723G/00 (1975).
Derwent Abstract WPI Acc No: 67-07987G/00 (1965).
Derwent Abstract WPI Acc No: 67-06359H/00 (1965).
Derwent Abstract WPI Acc No: 67-00989H/00 (1974).
Derwent Abstract WPI Acc No: 66-30706F/00 (1964).
Derwent Abstract WPI Acc No: 79-02867B [02] (1979).

*Primary Examiner*—Allen J. Robinson
*Attorney, Agent, or Firm*—Finnegan, Henderson, Farabow, Garrett & Dunner

[57] ABSTRACT

A method is disclosed for controlling macroinvertebrates in aqueous systems, such as lakes, comprising adding to the aqueous system in recognized need of such control an effective controlling amount of an anionic toxicant containing the anion $I^-$ or $F^-$, such as ethylenediamine (EDDI) or sodium fluoride (NaF).

8 Claims, 5 Drawing Sheets

METHOD FOR CONTROLLING MACROINVERTEBRATES

The present invention relates to a method for controlling macroinvertebrates, such as mollusks, in aqueous systems.

The chemical control of macroinvertebrate proliferation presently contributes to the degradation of water quality.

For instance, Smith (U.S. Pat. No. 4,462,914) used poly(quaternary ammonium) compounds, in particular, chlorides to control Asiatic clams. The poly(quaternary ammonium) compounds generally have a high cationic charge density and are fish and mollusk stressor toxicants which foul anionically charged gills. However, the poly(quaternary ammonium) compounds add undesirable chlorides to fresh waters which is viewed as a negative contributor to water quality management.

Whitekettle and Lyons (U.S. Pat. No. 4,970,239) killed mollusks with alkylthioalkylamines, in particular, decylthioethyl amine. However, the cationic properties of amines on gill plugging in fish and the contribution of sulfur to fresh waters are negative contributors to water quality management.

Allan and Hinton (British Patent 1,464,005) reported on the molluscicidal properties of poly(hexamethylene biguanide)-HCl. However, this compound is also a polycationic chemical which carries a large cationic mass which is believed to make it a fish killer as well as a molluscicide.

Sindery (French Patent 1,460,037) reported primary, secondary and tertiary amines to be molluscicidal. However, Sindery does not teach the advantages of using diamine-iodine salts over diamine-chlorine salts and also failed to teach the value of minimizing cationic charges on water treatment chemicals.

Nishimura et al. (Japanese Kokai 79/110,323) found N-monosubstituted propylenediamines to be molluscicidal to marine barnacles. However, cationic amines and diamines are irritants and gill fouling compounds which do not permit optimum water quality management in view of the negative effects on the fish population.

Kozianowski (Chemical Abstracts 65:4577g, 1966) reported the ethanolamine salts of 2,5-dichloro-4-nitrosalicylanilide to be effective for the control of snails. However, this compound is very costly and not affordable for water management systems in either underdeveloped or developed countries.

Shevtsova et al. (Chemical Abstracts 91:85169p, 1979) controlled the zebra clam in irrigation pipes with ammonium nitrate at concentrations of 400-500 ppm. Shevtsova et al. found control inadequate at cold temperatures (9°-11° C.) and also found yearling clams to be more resistant than younger or older clams. However, in water systems, both the cation and the anion of the ammonium nitrate compound contribute nitrogen to fresh waters which is less than optimum because the nitrogen contributes to both eutrophication and algal blooms.

Thornton, *Pulp & Paper*, pages 127-129, 1989, reported on the macro-fouling of paper mill waters by Asiatic clams and recommended cationic polyquats for the control of clam proliferation. However, the use of such cationic compounds is not acceptable as discussed above. Still, Thornton expressed the need for a safe, cost-effective, potent, EPA-approved molluscicide.

Monroe, reporting in *Time* magazine in January 1991, highlighted the problems created for industry, utilities, cities and individuals by zebra clam proliferation in the Great Lakes.

Accordingly, there are recognized problems associated with the proliferation of macroinvertebrates, such as mollusks. Further, previous attempts to control the proliferation have resulted in less than optimal environmental conditions associated with the discharges of waters treated with stressors and toxicants such as chlorine, bromine, potassium chloride, ammonium, copper and other heavy metals. Thus, there is a need for a better means of controlling macroinvertebrates.

The objects of the present invention are to effectively control macroinvertebrate proliferation, such as mollusk proliferation, in waters while, at the same time, reducing adverse effects on water quality and the environment.

Additional objects and advantages of the present invention will be set forth in part in the description which follows, and in part will be obvious from the description, or may be learned by the practice of the present invention. The objects and advantages of the present invention will be realized and attained by means of the elements and combinations particularly pointed out in the appended claims.

To achieve the objects and in accordance with the purpose of the present invention, as embodied and broadly described herein, the present invention comprises a method of controlling macroinvertebrates in aqueous systems which comprises adding to a system in recognized need of such control an effective controlling amount of at least one anionic toxicant which contains the anion iodide ($I^-$) or fluoride ($F^-$), such as ethylenediamine dihydriodide (EDDI) or sodium fluoride (NaF). In other words, the anionic toxicant used in the present invention is a water-soluble source of iodide or fluoride anion.

It is to be understood that both the foregoing general description and the following detailed description are exemplary and explanatory only and are not restrictive of the present invention, as claimed.

Figure 1:
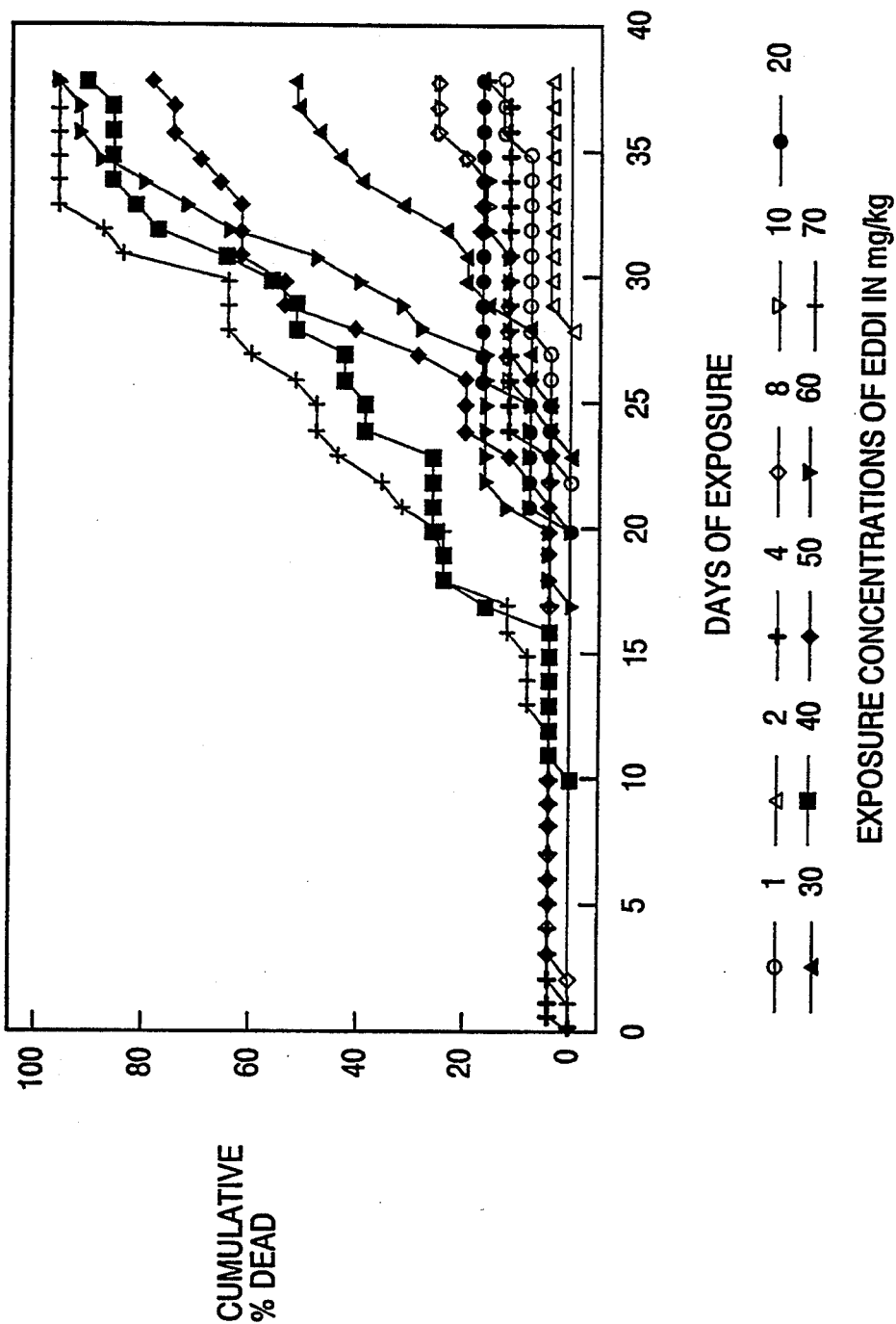
FIG. 1 sets forth the results of EDDI static exposure on Dreissena in terms of cumulative percent dead versus time of exposure.

The term "macroinvertebrates" as used herein, is defined as the classes of aquatic organisms that develop from a juvenile or larval life stage form to adult life stage forms. Macroinvertebrates are complex multi-cellular organisms containing an integration of organs and tissues that make up advanced life support systems (i.e., circulatory, digestive, reproductive, nervous).

It is the result of the development of the adult life stages of macroinvertebrates that causes many unique fouling problems to water systems, e.g., cooling systems. These problems are categorized under the term "macrofouling" and can result in damaged equipment, jeopardized safety related systems, and reduced line pressure, which can reduce cooling efficiency. Reduced cooling efficiency can jeopardize the system equipment and reduce overall efficiency and revenue. Further, it is understood that the term "macrofouling" also includes the degradation of aqueous systems, for instance, where the macroinvertebrates consume food sources such as plankton at the expense of the other aquatic life in the aqueous system.

It is also understood that the term "biofouling" means the occlusion of pipes or conduits used for the transport of either raw waters or treated waters by biomass from macroorganisms such as mollusks and attendant algae, protozoa, fungi and bacteria.

Exemplary macroinvertebrates include mollusks (i.e., clams, mussels, oysters and snails), crustaceans, sponges, annelids, bryozoans, and tunicates.

The present invention may be used for industrial plants and utilities which are subject to such macrofouling, whether the system is using water on a once-through basis or is of the recirculating type. The present invention may also be used for any aqueous source, such as lakes and swimming pools and potable water, which is in need of macrofouling and/or biofouling control. Preferably, the present invention is intended to control all life stages of the macroinvertebrates.

The use of anionic toxicants which contain the anion iodide ($I^-$) or fluoride ($F^-$) for controlling macroinvertebrates is encompassed by the present invention and preferred examples of such anionic toxicants include, but are not limited to, ethylenediamine dihydriodide (EDDI) and sodium fluoride (NaF). Other examples would include hydrogen fluoride and potassium fluoride.

Anionic toxicants, unlike cationic surfactants, affect macroinvertebrates via its anion rather than its cation. For instance, EDDI is approximately 79.5% anionic mass and only about 19.5% cationic mass. Further, the anionic toxicants, unlike chlorine and other irritants used for macroinvertebrate control, do not stress macroinvertebrates, meaning, for example, the mollusks do not withdraw into their shells but continue to filter-feed in the presence of the anion iodide or fluoride until their biological systems close down due to iodide or fluoride toxicity.

Anionic toxicants such as EDDI are environmentally preferable to cationic toxicants because fish and other aquatic life are not seriously affected and because the anionic toxicants contribute less nitrogen and subsequently less eutrophication to fresh waters.

In fact, one such anionic toxicant, EDDI, although not previously known for the control of macroinvertebrates, is already recognized as a safe compound to be used in aqueous systems since it is already a commercial product sold mostly for animal feeds and fish foods. Thus, its use in water treatment would not only help to cure an expanding water-quality problem, but also add needed iodine to the food chain in iodine deficient waters.

As a particular example and in accordance with the present invention, EDDI may be added to the desired aqueous system in recognized need of macrofouling control in an amount from about 1.0 ppm to about 100 ppm EDDI of the aqueous system to be treated. Preferably about 80 ppm to about 85 ppm of EDDI is added to the aqueous system in need of macrofouling control. EDDI is commercially available from West Agro, Inc., Kansas City, Mo. Generally, other anionic toxicants containing the anion $I^-$ could be added to the aqueous system in need of macrofouling control in the range of about 0.8 ppm $I^-$ to about 80 ppm $I^-$.

With respect to the sodium fluoride treatment, in accordance with the present invention, the sodium fluoride treatment may be added to the desired aqueous system in recognized need of macrofouling control, in an amount from about 0.5 ppm to about 10 ppm sodium fluoride of the aqueous system to be treated. Preferably, for northern aqueous systems about 2 ppm to about 3 ppm of sodium fluoride and, for southern waters, about 3 ppm to about 10 ppm of sodium fluoride, are added to the aqueous system in need of macrofouling control.

Generally, other anionic toxicants containing the anion $F^-$ could be added to the aqueous system in need of macrofouling control in the range from about 0.2 ppm $F^-$ to about 4.5 ppm $F^-$.

The present invention will be further clarified by the following examples, which are intended to be purely exemplary of the present invention and are not intended to restrict the scope thereof.

EXPERIMENT 1

Mussels were obtained from the Bay Metropolitan Water Treatment Plant at Bay City, Mich. Twenty mussels were placed in each of two 1000 ml graduated plastic beakers containing raw Saginaw Bay water. Using a 1X magnifier fitted over the tops of the beakers, the test mussels were viewed to determine if they were alive or dead. Upon review, adult-open-valve mussels, close-valve adults, empty shells of adults, open-valve yearlings, small and micromussels and black byssal fibers in a network between mature and yearling mussels were observed.

To one of the beakers, 2.5 ml of a stock solution containing 1000 ppm of NaF (5 ppm) was added and filled to the 500 ml level with raw Saginaw Bay water. To the other beaker, 40 ml of a stock solution containing 1000 ppm of EDDI (80 ppm) was added and also filled to the 500 ml level with raw Saginaw Bay water.

Control mussels were kept in a separate container of raw water and were observed from time to time under the magnifier.

Mussels under the sodium fluoride stress ceased movement within about five minutes after the treatment and those under EDDI stress moved for several more minutes and kept their valves open for four hours.

At the end of four hours, a mortality determination on the treated and control mussels was made. The determination was accomplished by inserting a number 12 crochet needle between the valves and determining whether or not the mussels closed their valves. The adult mussels in the raw, untreated water were alive and so were the yearlings. The small mussels were not probed.

The treated mussels which had been under stress by the test chemicals did not close their valves on the needle and all were classified as dead.

During the probing of the mussel valves, there was a difference in the brittleness of the valves. The valves of the mussels that had been under sodium fluoride stress were brittle and invariably broke during the probing. The valves of the controls and those which had been under EDDI stress were not brittle and none broke during the probing.

It is believed that there is a reaction between sodium fluoride and $CaCO_3$ in mussel shells ($CaCO_3 + 2\ NaF = Na_2CO_3 + CaF_2$) to form a brittle compound which can allow the shells to break apart. Based on these experimental results, the inventor is aware of no other molluscicide that will chemically attack the shells of the zebra mussels and kill them whether or not their shells are open.

EXPERIMENT 2

Snails, five per beaker, in 800 ml of Tennessee River water were exposed for four hours in different chemical concentrations ranging from zero to 100 ppm. Water temperatures were at ambient air temperatures.

Healthy, yearling animals were selected for the tests and were collected from submerged boulders and averaged from about 7 to 10 mm in diameter at the base of their shells.

TABLE 1

Numbers of dead snails after four hours of exposure to Ethylenediamine Dihydriodide (EDDI) and Methylglycoside at three concentrations, respectively, in Tennessee River water.

| Treatment | 10 ppm | 50 ppm | 100 ppm |
| --- | --- | --- | --- |
| Control | 0 | 0 | 0 |
| Methylglycoside | 0 | 0 | 0 |
| EDDI | 3 | 5 | 5* |

Observations during exposure revealed slow and lethargic movement by snails in control water. The snails in beakers treated with the relaxant methylglycoside were more active but still not stressed. The water temperature was 12° to 15° C., and temperature alone reduced mobility.

Snails in beakers containing water treated with EDDI were more active than controls and less active than those under methylglycoside treatment, but the EDDI treated snails were not irritated or stressed, and they did not enter into reclusion. Some of the snails did climb the beaker walls. Before death and falling, their feet changed color from a white to pink on bottom to a purple-orange, and there was a distortion of their feet.

The toxic snails never entered reclusion, and they became immobile and insensitive to stimuli. The immobilized snails were subjected to 500 ppm of glacial acetic acid to confirm immobility and death.

EXPERIMENT 3

As set forth in Table 2, further toxicity tests of EDDI on adult individuals of the Asian clam, *Corbicula fluminea* and the Zebra mussel, Driessina, were conducted. Table 2 also sets forth the amount of EDDI used as well as the number of Asian claim or Zebra mussels used in each experiment as well as the average time to mortality.

Figure 2:
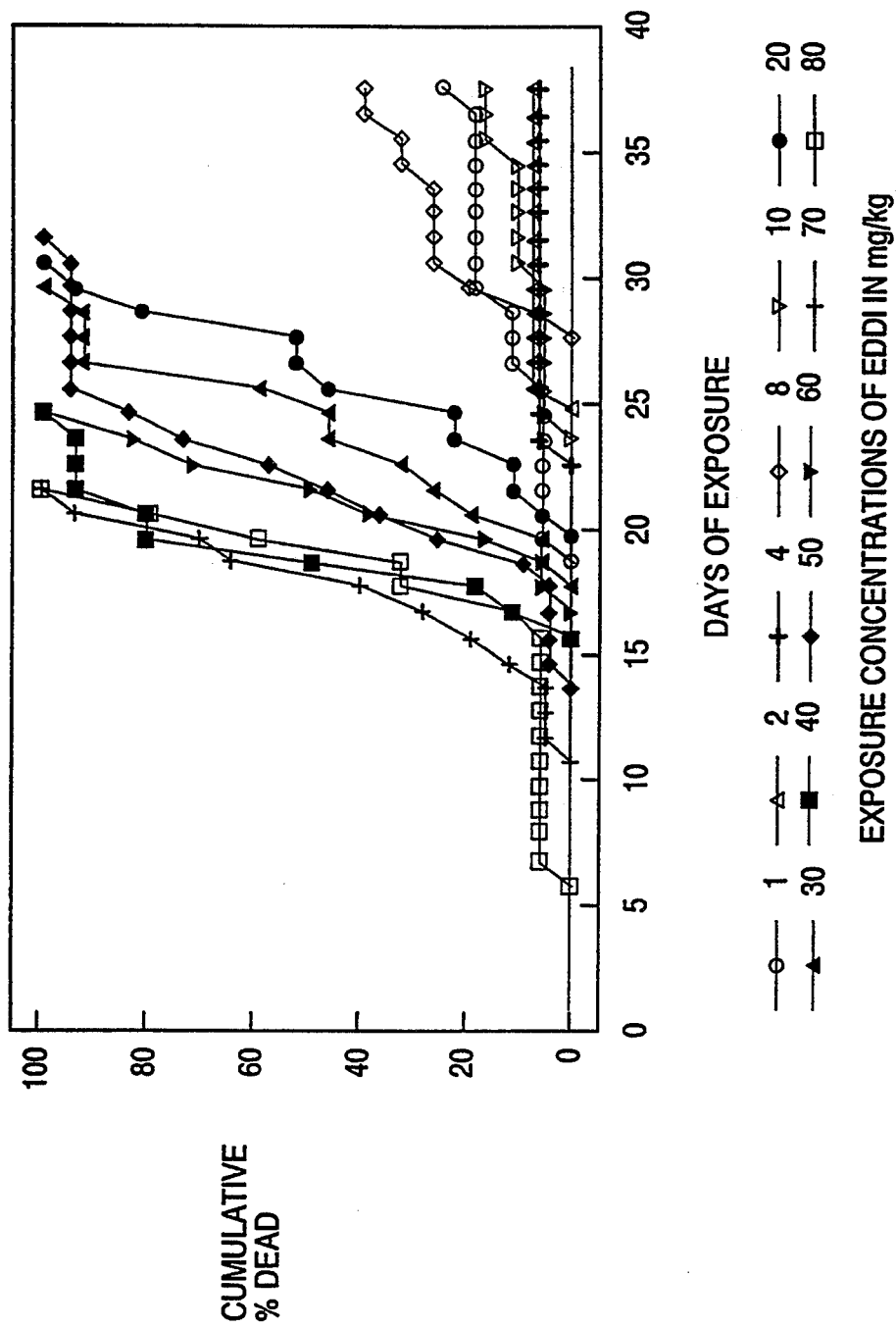
FIG. 2 sets forth the results of EDDI static exposure on Corbicula in terms of cumulative percent dead versus time of exposure.
Figure 3:
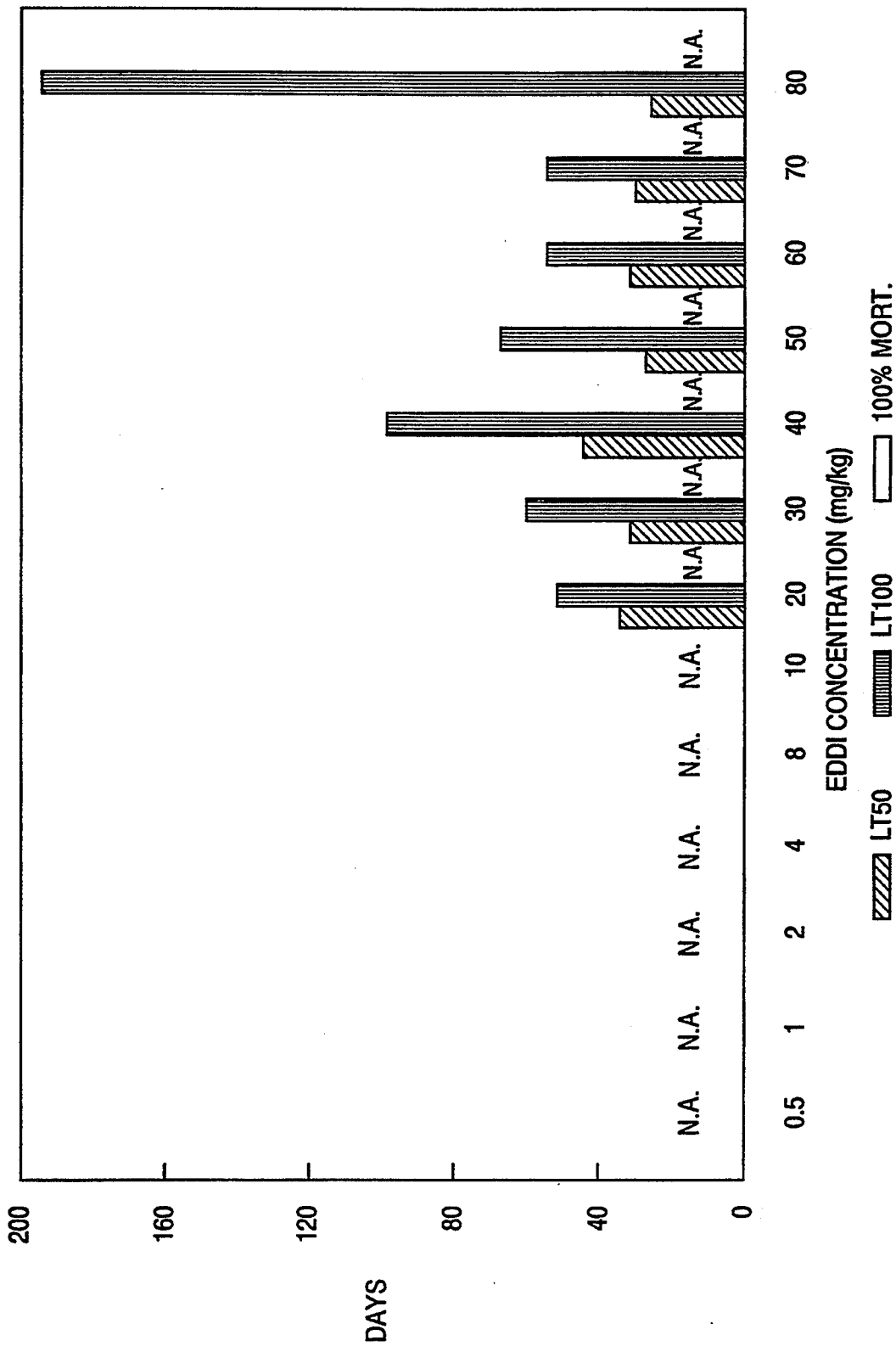
FIG. 3 sets forth the results of EDDI static exposure on Dreissena in terms of mortality rates based on varying EDDI concentrations.
Figure 4:
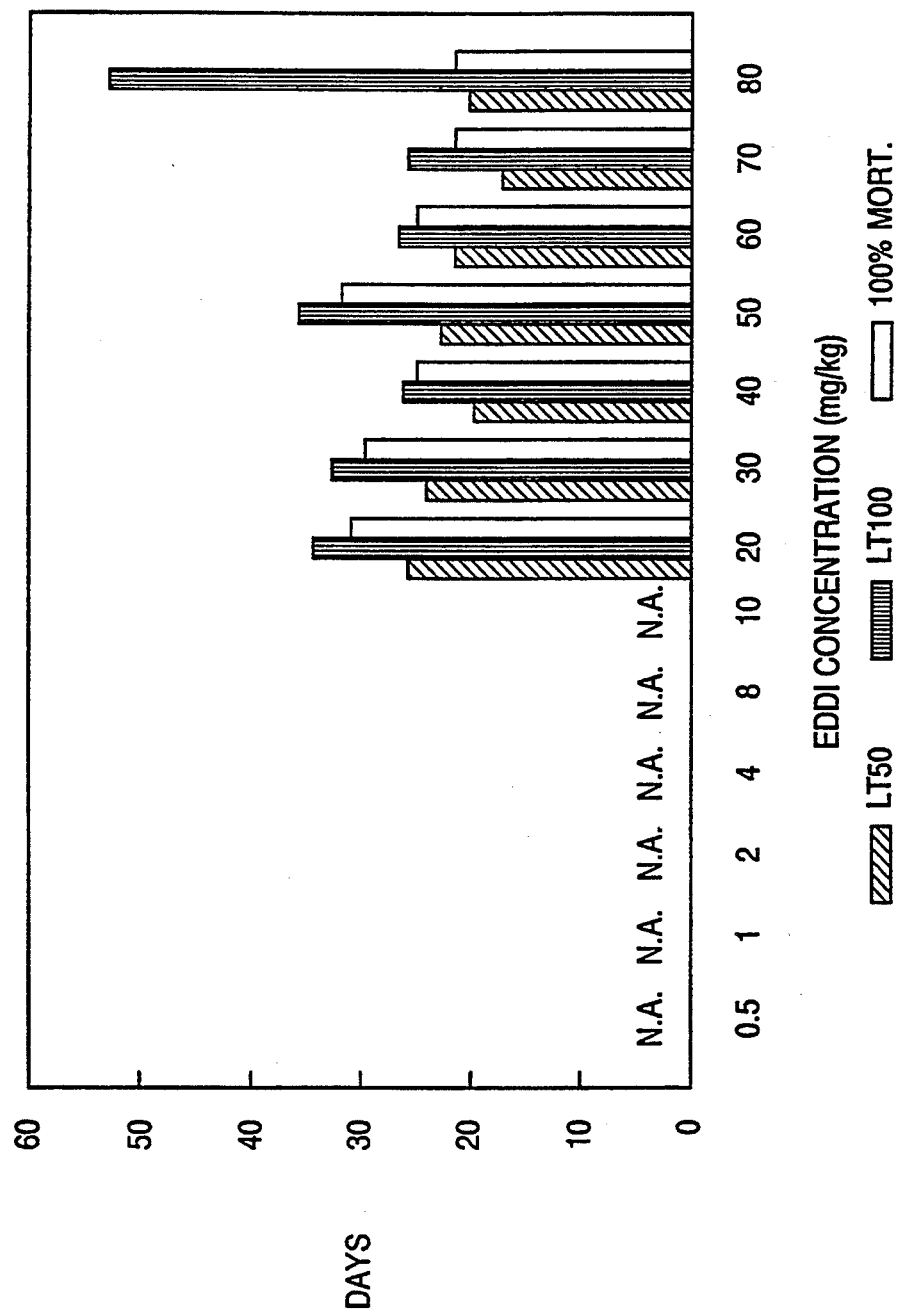
FIG. 4 sets forth the results of EDDI static exposure on Corbicula in terms of mortality rates based on varying EDDI concentrations.
Figure 5:
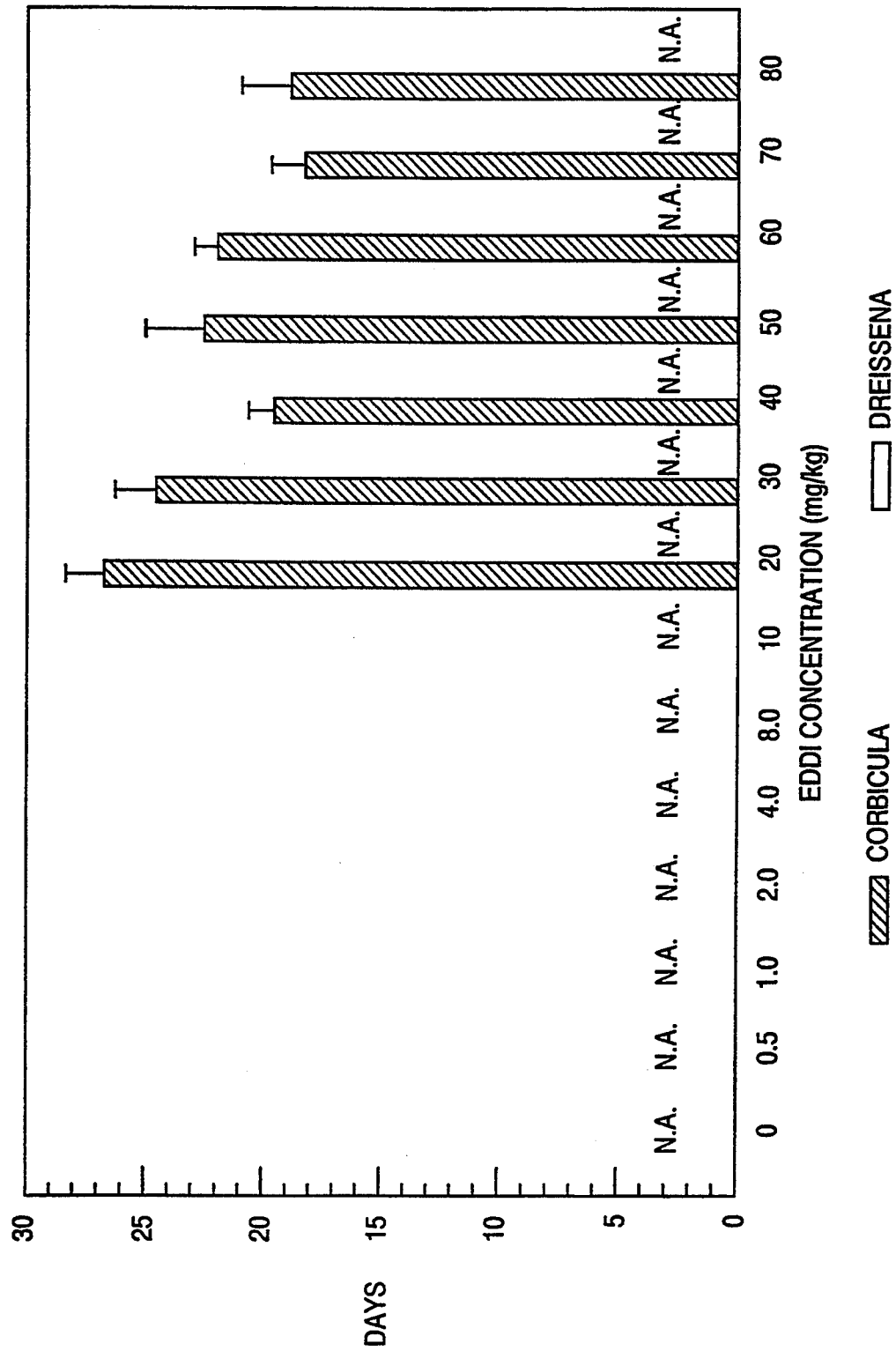
FIG. 5 sets forth the results of EDDI static exposure on Corbicula and Dreissena in terms of mean time to death based on varying EDDI concentrations.

The results in Table 2 are also graphically shown in FIGS. 1–5.

TABLE 2

Summary of results of toxicity tests of EDDI to adult individuals of the Asian clam, *Corbicula fluminea* and the Zebra mussel, *Dreissena polymorpha.*

| Treatment Level mg/kg | n | Mean Time to Death (Days) | s.d. | 95% Confidence Limits (Days) | Range (Days) | Test Range Effect AMOVA | Size Effect $LT_{50}$ (Yes/No) | $LT_{100}$ (Days) | $MT_{100}$ (Days) | (Days) |
| --- | --- | --- | --- | --- | --- | --- | --- | --- | --- | --- |
| *Corbicula fluminea* | | | | | | | | | | |
| Control | 16 | (0% dead after 37.83 days of exposure) | | | | N.A.* | — | | | |
| 0.5 mg/kg | 15 | (0% dead after 37.83 days of exposure) | | | | N.A. | — | | | |
| 1.0 mg/kg | 16 | (25% dead after 37.83 days of exposure) | | | | N.A. | — | 38.96 | 78.48 | — |
| 2.0 mg/kg | 13 | (6% dead after 37.83 days of exposure) | | | | N.A. | — | 249.09 | 3204.55 | — |
| 4.0 mg/kg | 15 | (7% dead after 37.83 days of exposure) | | | | N.A. | — | 566.40 | 15432.36 | — |
| 8.0 mg/kg | 15 | (40% dead after 37.83 days of exposure) | | | | N.A. | — | 36.21 | 51.92 | — |
| 10.0 mg/kg | 18 | (17% dead after 37.83 days of exposure) | | | | N.A. | — | 40.01 | 65.02 | — |
| 20.0 mg/kg | 17 | 26.76 | ±2.93 | ±1.51 | 20.83–30.83 | | No | 25.81 | 34.67 | 30.83 |
| 30.0 mg/kg | 15 | 24.56 | ±3.02 | ±1.67 | 18.90–29.82 | | No | 24.21 | 38.68 | 29.82 |
| 40.0 mg/kg | 16 | 19.61 | ±1.97 | ±1.05 | 16.83–24.87 | See | No | 19.67 | 26.22 | 24.87 |
| 50.0 mg/kg | 19 | 22.57 | ±5.22 | ±2.52 | 14.81–31.90 | Following | No | 22.90 | 35.83 | 31.90 |
| 60.0 mg/kg | 18 | 22.11 | ±1.96 | ±0.97 | 17.88–24.87 | Table 2a | No | 21.57 | 26.53 | 24.87 |
| 70.0 mg/kg | 17 | 18.38 | ±2.57 | ±1.32 | 11.90–21.81 | | No | 17.49 | 25.80 | 21.81 |
| 80.0 mg/kg | 15 | 18.97 | ±3.71 | ±2.05 | 6.38–21.81 | | No | 20.73 | 83.05 | 21.81 |
| *Dreissena polymorpha* | | | | | | | | | | |
| Control | 25 | (0% dead after 37.83 days of exposure) | | | | N.A. | — | | | |
| 0.5 mg/kg | 25 | (0% dead after 37.83 days of exposure) | | | | N.A. | — | | | |
| 1.0 mg/kg | 23 | (13% dead after 37.83 days of exposure) | | | | N.A. | — | 55.64 | 130.06 | — |
| 2.0 mg/kg | 25 | (4% dead after 37.83 days of exposure) | | | | N.A. | — | 221.64 | 170.43 | — |
| 4.0 mg/kg | 24 | (16% dead after 37.83 days of exposure) | | | | N.A. | — | 234.88 | 38559.21 | — |
| 8.0 mg/kg | 24 | (25% dead after 37.83 days of exposure) | | | | N.A. | — | 151.24 | 4075.62 | — |
| 10.0 mg/kg | 23 | (17% dead after 37.83 days of exposure) | | | | N.A. | — | 39.20 | 84.13 | — |
| 20.0 mg/kg | 25 | (52% dead after 37.83 days of exposure) | | | | N.A. | — | 35.25 | 53.02 | — |
| 30.0 mg/kg | 24 | (68% dead after 37.83 days of exposure) | | | | N.A. | — | 32.65 | 60.30 | — |
| 40.0 mg/kg | 25 | (36% dead after 37.83 days of exposure) | | | | N.A. | — | 43.93 | 99.02 | — |
| 50.0 mg/kg | 23 | (91% dead after 37.83 days of exposure) | | | | N.A. | — | 26.93 | 67.47 | — |
| 60.0 mg/kg | 24 | (79% dead after 37.83 days of exposure) | | | | N.A. | — | 30.92 | 54.87 | — |
| 70.0 mg/kg | 25 | (96% dead after 37.83 days of exposure) | | | | N.A. | — | 29.60 | 53.48 | — |
| 80.0 mg/kg | 25 | (96% dead after 37.83 days of exposure) | | | | N.A. | — | 26.63 | 192.68 | — |

*N.A. (not applicable) indicates value could not be calculated as not all individuals in the sample died during the exposure period.

TABLE 2A

Summary of One-way analysis of variance testing the difference in mean times to death in Asian clams (*Corbicula fluminea*) displaying 100% sample mortality on exposure to EDDI within the total test period of 37.83 days (i.e., treatment levels of 20, 30, 40, 50, 60, 70, and 80 mg EDDI/kg solution.

| Treatment Level mg/kg | n | Mean Time to Death (Days) | s.d. | 95% Confidence Limits (Days) | Range (Days) | Range* Test AMOVA | Size Effect (Yes/No) | $LT_{50}$ (Days) | $LT_{100}$ (Days) | $MT_{100}$ (Days) |
|---|---|---|---|---|---|---|---|---|---|---|
| *Corbicula fluminea* | | | | | | | | | | |
| 20.0 mg/kg | 17 | 26.76 | 2.93 | 1.5 | 20.83–30.83 | | | No | 25.91 | 34.67 | 30.83 |
| 30.0 mg/kg | 15 | 24.56 | 3.02 | 1.6 | 18.90–29.82 | | | | No | 24.21 | 28.68 | 29.82 |
| 50.0 mg/kg | 19 | 22.57 | 5.22 | 2.5 | 14.81–31.90 | | | No | 22.90 | 25.83 | 31.90 |
| 60.0 mg/kg | 18 | 22.11 | 1.96 | 0.9 | 17.88–24.87 | | | | No | 21.57 | 26.53 | 24.87 |
| 40.0 mg/kg | 16 | 19.61 | 1.97 | 1.5 | 16.83–24.87 | | | | No | 19.67 | 26.22 | 24.87 |
| 80.0 mg/kg | 15 | 18.97 | 3.71 | 2.0 | 6.88–21.81 | | | No | 20.73 | 53.05 | 21.81 |
| 70.0 mg/kg | 17 | 18.38 | 2.57 | 1.5 | 11.90–21.81 | | | No | 17.49 | 25.80 | 21.81 |

*Vertical lines running across mean times to death are indicative of no significant dofference among those means ($P > 0.05$). Means not connected by vertical lines are significantly different from each other ($P < 0.05$) as tested by a one-way analysis of variance. For a descriptive summary of these results see test below.

SUMMARY OF AMOVA TESTING OF MEAN TIMES TO DEATH ON EXPOSURE TO EDDI FOR *CORBICULA FLUMINEA*.
Mean time to death at 20 mg EDDI/kg is significantly different from means at 40, 50, 60, 70 and 80 mg/kg but not from 30 mg/kg.
Mean time to death at 30 mg EDDI/kg is significantly different from means at 40, 70 and 80 mg/kg but not from 20, 30, 50, and 60 mg/kg.
Mean time to death at 40 mg EDDI/kg is significantly different from means at 20, 30 and 50 mg/kg but not from 60, 70 and 80 mg/kg.
Mean time to death at 50 mg EDDI/kg is significantly different from means at 20, 40, 70 and 80 mg/kg but not from 30 and 60 mg/kg.
Mean time to death at 60 mg EDDI/kg is significantly different from means at 20, 70 and 80 mg/kg but not from 30, 40 and 50 mg/kg.
Mean time to death at 70 mg EDDI/kg is significantly different from means at 20, 30, 50 and 60 mg/kg but not from 40 and 80 mg/kg.
Mean time to death at 80 mg EDDI/kg is significantly different from means at 20, 30, 50 and 60 mg/kg but not from 40 and 70 mg/kg.

As can be seen from the above experiments, sodium fluoride and EDDI are quite effective as molluscicides.

Other embodiments of the invention will be apparent to those skilled in the art from consideration of the specification and the practice of the invention disclosed herein. It is intended that the specification and examples be considered at exemplary only, with a true scope and spirit of the invention being indicated by the following claims.

What is claimed is:

1. A method for controlling macroinvertebrates in an aqueous system comprising adding to said aqueous system in recognized need of such control an effective toxic controlling amount of ethylenediamine dihydriodide wherein said ethylenediamine dihydriodide is added in the amount of from about 1.0 ppm to about 100 ppm in said aqueous system.

2. The method of claim 1 wherein said macroinvertebrates are selected from the group consisting of clams, mussels, and snails.

3. The method of claim 1 wherein said macroinvertebrates are mollusks.

4. The method of claim 3 wherein said mollusks are selected from the group consisting of Asiatic clams and Zebra mussels.

5. A method for controlling macroinvertebrates in an aqueous system comprising adding to said aqueous system in recognized need of such control an effective toxic controlling amount of ethylenediamine dihydriodide.

6. The method of claim 5 wherein said macroinvertebrates are selected from the group consisting of clams, mussels, and snails.

7. The method of claim 5 wherein said macroinvertebrates are mollusks.

8. The method of claim 7 wherein said mollusks are selected from the group consisting of Asiatic clams and Zebra mussels.

* * * * *